United States Patent [19]

Van Kamp et al.

[11] 3,937,700

[45] Feb. 10, 1976

[54] NOVEL 1,2-METHYLENE-17α-ACYLOXY (OR IMPROVED HYDROXY)-9β, 10α-STEROID COMPOUNDS OF THE PREGNANE SERIES, PHARMACEUTIC PREPARATIONS ON THE BASIS OF THE NOVEL COMPOUNDS AND METHODS OF PRODUCING SAID COMPOUNDS AND PREPARATIONS

[75] Inventors: Harmen Van Kamp; Pieter Westerhof; Lucas Morsink, all of Weesp, Netherlands

[73] Assignee: U.S. Philips Corporation, New York, N.Y.

[22] Filed: July 18, 1973

[21] Appl. No.: 380,196

Related U.S. Application Data

[63] Continuation of Ser. No. 120,705, March 3, 1971, abandoned.

[30] Foreign Application Priority Data

Mar. 4, 1970 Netherlands....................... 7003064

[52] U.S. Cl. 260/239.55 R; 260/397.4; 260/397.47; 260/397.5; 424/243
[51] Int. Cl.$^2$........................................... C07J 17/00
[58] Field of Search ........................... 260/239.55 R

[56] References Cited
UNITED STATES PATENTS

| | | | |
|---|---|---|---|
| 3,423,433 | 1/1969 | Westerhof........................ | 260/397.3 |
| 3,423,507 | 1/1969 | Neri.................................. | 424/243 |

*Primary Examiner*—Elbert L. Roberts
*Attorney, Agent, or Firm*—Frank R. Trifari; Norman N. Spain

[57]  ABSTRACT

New 1,2-methylene-17α acyloxy-9β, 10α pregnane compounds having high progestational and anti-ovulatory activities.

14 Claims, No Drawings

NOVEL 1,2-METHYLENE-17α-ACYLOXY (OR IMPROVED HYDROXY)-9β, 10α-STEROID COMPOUNDS OF THE PREGNANE SERIES, PHARMACEUTIC PREPARATIONS ON THE BASIS OF THE NOVEL COMPOUNDS AND METHODS OF PRODUCING SAID COMPOUNDS AND PREPARATIONS

This is a continuation of application Ser. No. 120,705, filed Mar. 3, 1971, now abandoned.

From the Applicant's U.S. Pat. No. 3,198,792 is known that the steroids of the retroseries having, in contrast to the steroids of the normal series, a 9,β,10α-configuration, having interesting, endocrinological properties.

As examples of retro-steroids the columns 11 to 23 of said Patent Specification indicate about 800 substances or groups of substances.

It has now been found that 9,β,10α-steroids corresponding to the general formula:

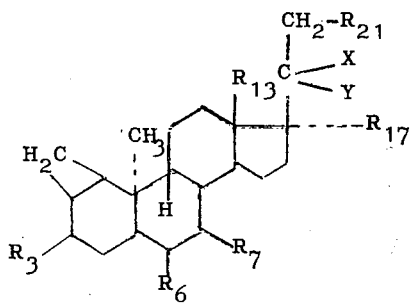

in which X and y in common represent a double-bonded oxygen atom or X is a hydrogen atom and y is a hydroxy-group or an esterified hydroxy group, $R_3$ is a 3-keto-4-dehydro-,
3-keto-4,6-bisdehydro-,
3-OR'-3,5-bisdehydro- or
a 3-OR'-4,6-bisdehydro-group, OR' representing an etherified or esterified hydroxy-group, $R_6$ is a hydrogen atom, a chlorine atom, a fluorine atom, a 6,6-difluoro-group, a 6,6-dichloro-group or a methyl-group, whilst is $R_6$ is a hydrogen atom $R_7$ represents a 6,7-methylene-group, $R_7$ is a hydrogen atom or a 6,7-methylene-group, whilst if $R_7$ is 6,7-methylene-group $R_6$ is a hydrogen atom, a chlorine atom or a fluorine atom and $R_3$ is a 3-keto-4-dehydro-group, $R_{17}$ is an etherified hydroxy-group having 1 to 5 carbon atoms or an esterified hydroxy-group having 1 to 8 carbon atoms, $R_{21}$ is a hydrogen atom, a fluorine atom, a hydroxy-group or an esterified hydroxy-group and $R_{13}$ is a methyl- or an ethyl-group, exhibit extremely high endocrinological activity.

The endocrinological activities and particularly the progestational and anti-ovolatory activity of the above-mentioned group of compounds according to the invention is considerably higher than than of the compounds mentioned in columns 11 to 23 of said patent Specification. it has furthermore been found that the progestational and anti-ovulatory activity of the substances according to the invention is many times higher than that of the isomeric compounds of the normal series.

It has particularly been found that the compounds corresponding to the general formula:

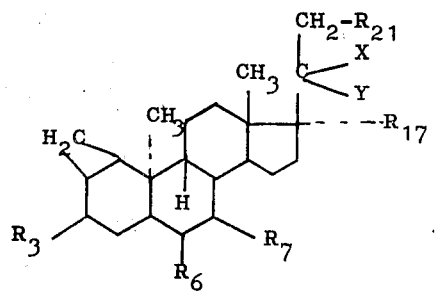

in which $R_3$, $R_6$, $R_7$, $R_{17}$, $R_{21}$, X and Y have the aforesaid meanings exhibit a surprisingly high progestational and anti-ovulatory activity.

This applies in particular to compounds of the formula:

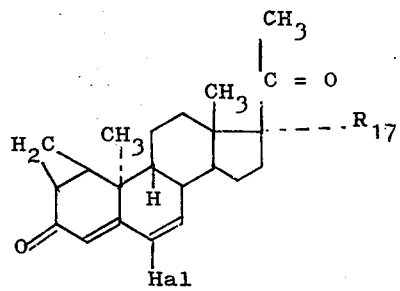

in which Hal is a chlorine atom or a fluorine atom and $R_{17}$ has the aforesaid meaning.

Very highly active compounds whose oral and parenteral progestational and anti-ovulatory activity is considerably higher than that of the strongest progestational and anti-ovulatory compounds hither to known are inter-alia:

1,2-methylene-6-chloro-17α-hydroxy-9β,10α-pregna-4,6-diene-3,20-dione 17-acetate, 1,2-methylene-6-fluoro-17α-hydroxy-9β,10α-pregna-1,6-dien-3,20-dione 17-acetate, 1,2-methylene-6-fluoro-17α-hydroxy-9β, 10α-pregna-4,6-diene-3,20-dione 17-propionate, 1,2-methylene-6-chloro-17α-hydroxy-9β,10α-pregna-4,6-diene-3,20 -dione 17-propionate, A considerably prolonged progestational and anti-ovulatory activity has been found with compounds of the formula:

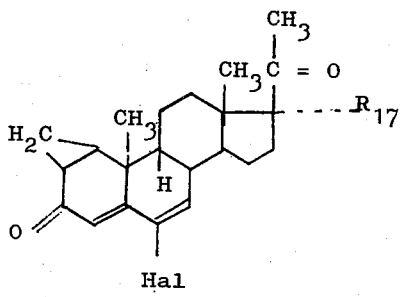

in which Hal is a fluoro- or chlorine atom and $R_{17}$ is an etherified hydroxy-group having 1 to 5 carbon atoms or an esterified hydroxy-group having 4 to 8 carbon atoms.

This applies in particular to the compounds;
1,2-methylene-6-chloro-17α-tetrahydropyranyloxy-9β,10α-pregna-4,6-diene-3,20-dione,
1,2-methylene-6-fluoro-17α-tetrahydropyranyloxy-9β,10α-pregna-4,6-diene-3,20-dione,
1,2-methylene-6-fluoro-17α-methoxy-9β,10α-pregna-4,6-diene-3,20-dione
1,2-methylene-6-chloro-17α-methoxy-9β,10α-pregna-4,6-diene-3,20-dione,
1,2-methylene-6-chloro-17α-hydroxy-9β,10α-pregna-4,6-diene-3,20-dione 17-caproate,
1,2-methylene-6-fluoro-17α-hydroxy-9β,10α-pregna-4,6-diene-3,20-dione 17-caproate, Apart from the aforesaid specific substances further examples of the active compounds according to the invention are:
1,2;6,7-bismethylene-17α-hydroxy-9β,10α-pregna-4-ene-3,20-dione 17-acetate,
1,2;6,7-bismethylene-6α-chloro-17α-hydroxy-9β,10α-pregna-4-ene-3,20-dione 17-acetate,
1,2;6,7-bismethylene--6α-fluoro-17α-hydroxy-9β,10α-pregna-4-ene-3,20-dione 17-acetate,
1,2-methylene-6,6-difluoro-17α-hydroxy-9β,10α-pregna-4-ene-3,20-dione 17-acetate,
1,2-methylene-6-chloro-17α-20β-dihydroxy-9β,10α-pregna-4,6-diene-3-one 17-acetate,
1,2-methylene-6-fluoro-17α,20β-dihydroxy-9β,10α-pregna-4,6-diene-3-one 17-acetate,
1,2-methylene-6-fluoro-17α,20β-dihydroxy-9β,10α-pregna-4,6-diene-3-one 17,20-diacetate,
1,2-methylene-6-chloro-17α,20β-dihydroxy-9β,10α-pregna-4,6-diene-3-one 17,20-diacetate,
1,2-methylene-6-methyl-17α-hydroxy-9β,10α-pregna-4,6-diene-3,20-dione 17-acetate,
1,2-methylene-3-ethoxy-6-chloro-17α-hydroxy-9β,10α-pregna-3,5-diene-20-one 17-acetate,
1,2-methylene-3-ethoxy-6-fluoro-17α-hydroxy-β,10α-pregna-3,5-diene-20-one 17-acetate,
6-chloro-3,7α-dihydroxy-1,2-methylene-9β,10α-pregna-4,6-diene-20-one 3,17-diacetate,
1,2-methylene-6-chloro-3β,17α-20β-trihydroxy-9β,10α-pregna-4,6-diene-17,20-triacetate,
1,2-methylene-6-fluoro-3β,17α,20β-trihydroxy-9β,10α-pregna-4,6-diene-3,17,20-triacetate,
1,2-methylene-6-chloro-17α-hydroxy-21-fluoro-9β,10α-pregna-4,6-diene-3,20-dione 17-acetate,
1,2-methylene-6-fluoro-17α-hydroxy-21-fluoro-9β,10α-pregna-4,6-diene-3,20-dione 17-acetate,
1,2-methylene-6-chloro-17α-methoxy-9β,10α-pregna-4,6-diene-3,20-dione,
1,2-methylene-6-fluoro-17β-methoxy-9β,10α-pregna-4,6-diene-3,20-dione,
1,2-methylene-6-fluoro-17α-propoxy-9β,10α-pregna-4,6-diene-3,20-dione,
1,2-methylene-6-chloro-17α-propoxy-9β,10α-pregna-4,6-diene-3,20 -dione, Other interesting compounds according to the invention are:
1,2-methylene-6β-fluoro-17α-hydroxy-9β,10α-pregna-4-ene-3,20-dione 17-acetate,
1,2-methylene-6β-chloro-17α-hydroxy-9β,10α-pregna-4-ene-3,20-dione 17-acetate,
1,2-methylene-6β-chloro-17α-hydroxy-9β,10α-pregna-4-ene-3,20-dione 17-propionate,
1,2-methylene-6β-fluoro-17α-hydroxy-9β,10α-pregna-4-ene-3,20 -dione 17-propionate,
1,2-methylene-6β-fluoro-17α-tetrahydropyranyloxy-9β,10α-pregn-4-ene-3,20-dione,
1,2-methylene-6β-chloro-17α-tetrahydropyranyloxy-9β,10α-pregn-4-ene-3,20-dione,
1,2-methylene-6β-chloro-17α-hydroxy-9β,10α-pregn-4-ene-3,20-dione 17-caproate,
1,2-methylene-6β-fluoro-17α-hydroxy-9β,10α-pregn-4-ene-3,20-dione 17-caproate,
1,2-methylene-6-chloro-17α,21-dihydroxy-9β,10α-pregna-4,6-diene-3,20-dione 17,21-diacetate,
1,2-methylene-6-fluoro-17α-21-dihydroxy-9β,10α-pregna-4,6-diene-3,20-dione 17,21-diacetate,
1,2-methylene-6,6-dichloro-17α-hydroxy-9β,10α-pregn-4-ene-3,20-dione 17-acetate,
1,2-methylene-6-fluoro-17α-hydroxy-18-methyl-9β,10α-pregna-4,6-diene-3,20-dione 17-acetate,
1,2-methylene-6-chloro-17α-hydroxy-18-methyl-9β,10α-pregna-4,6-diene-3,20-dione 17-acetate,
1,2-methylene-6-chloro-17α-hydroxy-18-methyl-9β,10α-pregna-4,6-diene-3,20-dione 17propionate,
1,2-methylene-6-fluoro-17α-hydroxy-18-methyl-9β,10α-pregna-4,6-diene-3,20-dione 17-propionate,
1,2-methylene-6-fluoro-17α-tetrahydropyranyloxy-18-methyl-9β,10α-pregna-4,6-diene-3,20-dione,
1,2-methylene-6-chloro-17α-tetrahydropyranyloxy-18-methyl-9β,10α-pregna-4,6-diene-3,20-dione,
1,2-methylene-6-chloro-17α-hydroxy-18-methyl-9β,10α-pregna-4,6-diene-3,20-dione 17-caproate,
1,2-methylene-6-fluoro-17α-hydroxy-18-methyl-9β,10α-pregna-4,6-diene-3,20-dione 17-caproate.

If the substituent $R_3$, Y or $R_{21}$ contains or represents a hydroxy-group, this group has 1 to 20 carbon atoms and is preferably derived from a saturated or unsaturated aliphatic mono-, di- or tricarboxylic acid, an alicyclic carboxylic accid, a mixed aliphatic-alicyclic carboxylic acid, an aliphatic-aromatic carboxylic acid, or an aromatic carboxylic acid. Examples of esterified hydroxy-groups are hydroxy-groups esterified with formic acid, acetic acid, propionic acid, butyric acid, decane carboxylic acid, cyclohexylpropionic acid, phenylpropionic acid, phenylacetic acid, phenyloxyphenylpropionic acid, enanthoylacetic acid, oleic acid, palmitinic acid, stearic acid, enanthoinic acid, capronic acid, pivalinic acid, succinic acid, malonic acid, banzoic acid, citric acid, p-hexyloxyphenylpropionic acid, hexahydrobenzoic acid, β-cyclopentylpropionic acid and βcyclohexylpropionic acid.

If $R_{17}$ is an esterified hydroxy-group, this group is derived from a carboxylic acid as mentioned above, but the acid must contain not more than 8 carbon atoms at the most. Suitable esterified hydroxy-groups are, for example, acetoxy, propionoxy and capronoxy.

If $R_3$ is an etherified hydroxy-group, this group is preferably derived from an aliphatic, a mixed aliphatic-aromatic, an mixed aliphatic-alicyclic alcohol. Examples of etherified hydroxy-groups are: methoxy, ethoxy, t-butoxy, cyclohexyloxy, benzyloxy, tetrahydrofuranyloxy, tetrahydropyranyloxy.

If $R_{17}$ is an etherified hydroxy-group, this group is derived from an alcohol of the kind mentioned above, on the understanding that the alcohol is allowed to contain five carbon atoms at the most. Suitable etherified hydroxy-groups are, for example, methoxy, ethoxy, propoxy, tetrahydropyranyloxy. It should furthermore be noted for the sake of clarity that the 1,2-methylene-group contained in the compounds according to the invention occupies the β-position.

The compounds according to the invention are novel substances which can be produced by methods known for the production of similar compounds or by analogous methods.

The compounds according to the invention may be produced by;

a. treating a compound of the formula:

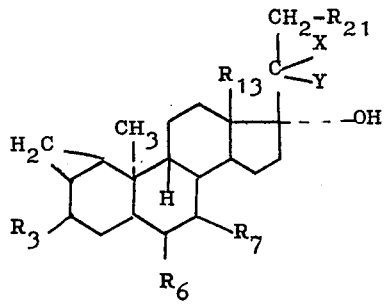

wherein $R_6$, $R_7$, $R_{13}$, $R_{21}$, X and Y have the aforesaid meanings and $R_3$ is a 3-keto-4-dehydro, or a 3-keto-4,6-bisdehydro-group, with an alkylating or acylating agent, which results in a compound of the formula

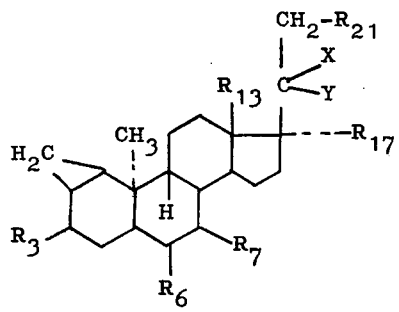

wherein $R_3$, $R_6$, $R_7$ and $R_{13}$ have the aforesaid meanings, $R_{17}$ has the above-mentioned meaning, X and Y represent in common a double-bonded oxygen atom or X is a hydrogen atom and Y is an esterified hydroxy-group, $R_{21}$ is a hydrogen atom, a fluorine atom or an esterified hydroxy-group, b. treating a compound of the formula:

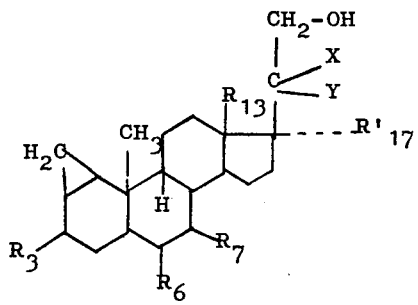

wherein $R_6$, $R_7$ and $R_{13}$ have the aforesaid meanings, $R_3$ is a 3-keto-4-dehydro-, or a 3-keto-4,6-bisdehydro-group, X and Y in common represent a double-bonded oxygen atom or X is a hydrogen atom and Y a hydroxy-group and $R'_{17}$ is a hydroxy-group or an etherified hydroxy-group having 1 to 5 carbon atoms or an esterified hydroxy-group having 1 to 8 carbon atoms, with an acylating agent, which results in a compound of the formula:

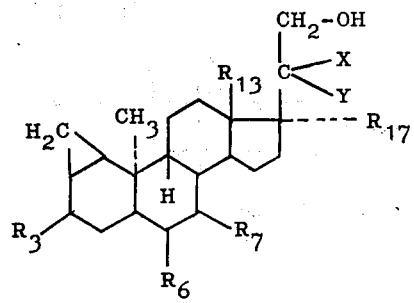

wherein $R_3$, $R_6$, $R_7$ and $R_{13}$ have the aforesaid meanings, $R_{17}$ has the aforesaid meaning, X and Y in common represent a double-bonded oxygen atom or X is a hydrogen atom and Y an esterified hydroxy-group and OR represents an acyloxy-group, c. treating a compound of the formula:

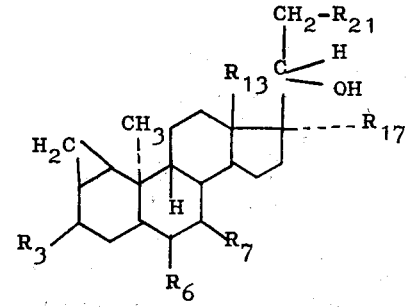

in which $R_6$, $R_7$, $R_{13}$ and $R_{17}$ have the above-mentioned meanings, $R_3$ is a 3-keto-4-dehydro-, a 3-keto-4,6-bisdehydro- or a 3-OH-4,6-bisdehydro-group and $R_{21}$ is a hydrogen atom, a fluorine atom or a hydroxy-group, with an acylating agent, which results in a compound of the formula:

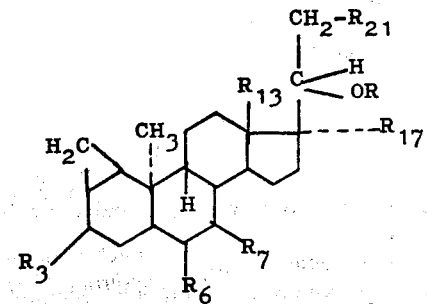

in which
R$_6$, R$_7$, R$_{13}$ and R$_{17}$ have the aforesaid meanings,
R$_3$ is a 3-keto-4-dehydro-,
3-keto-4,6-bisdehydro- or
3-OR'-4,6-bisdehydro-group,
OR' being an esterified hydroxy-group.
R$_{21}$ is a hydrogen atom, a fluorine atom or an esterified hydroxy-group and
OR is an acyloxy-group,
d. treating a compound of the formula:

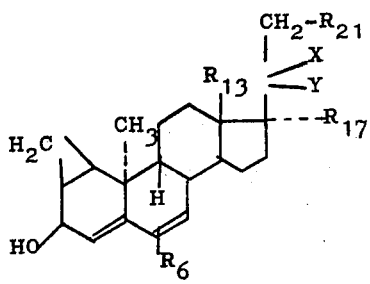

wherein R$_{13}$, R$_{17}$, R$_{21}$, X and Y have the aforesaid meanings and R$_6$ is a chlorine atom, a fluorine atom or a methyl-group,
with an alkylating or an acylating agent, which results in a compound of the formula:

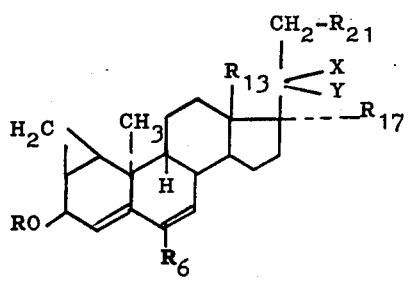

wherein
R$_6$, R$_{13}$, R$_{17}$, R$_{21}$, X and Y have the above-mentioned meanings,
OR is an etherified or an esterified hydroxy-group,
e. subjecting a compound of the formula:

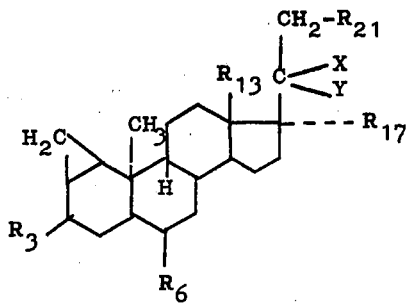

wherein
R$_{13}$, R$_{17}$, R$_{21}$, X and Y have the above-mentioned meanings,
R$_3$ is a 3-keto-4-dehydro- or
a 3-OR'-3,5-bisdehydro-group, OR' being an etherified or an esterified hydroxy-group and R$_6$ is a chlorine atom, a fluorine atom or a methyl-group, to a 6,7-dehydrating reaction, which results in a compound of the formula:

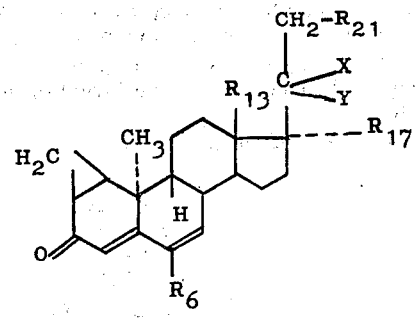

wherein R$_6$, R$_{13}$, R$_{17}$, R$_{21}$, X and Y have the above-mentioned meanings,
f. subjecting a compound of the formula:

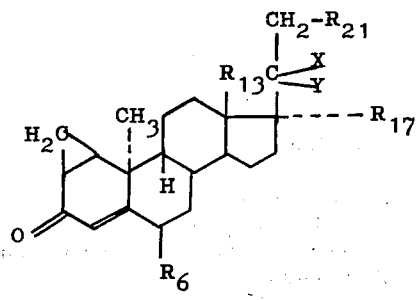

in which
R$_{13}$, R$_{17}$, R$_{21}$, X and Y have the abovementioned meanings,
R$_6$ is a chlorine atom, a fluorine atom or a methyl-group, to an enol-etherification or an enol-esterification, which results in a compound of the formula:

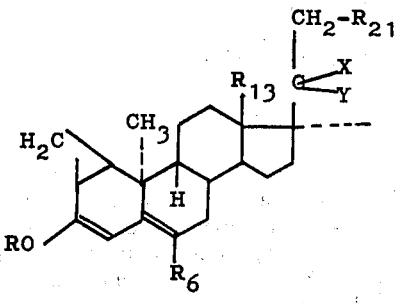

in which
R$_6$, R$_{13}$, R$_{17}$, R$_{21}$, X and Y have the aforesaid meanings and
OR is an etherified or an esterified hydroxy-group,
g. treating a compound of the formula:

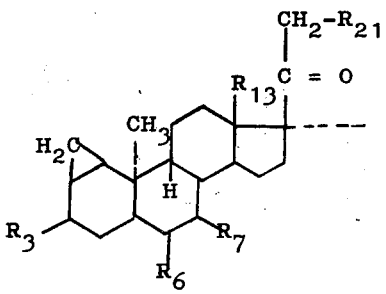

in which
R$_6$, R$_7$, R$_{13}$, R$_{17}$ and R$_{21}$ have the above-mentioned meanings and
R$_3$ is a 3-keto-4-dehydro- or
a 3-keto-4,6-bisdehydro-group,
with a reducing agent, the corresponding 20-hydroxy-compound being obtained, h. treating a compound of the formula:

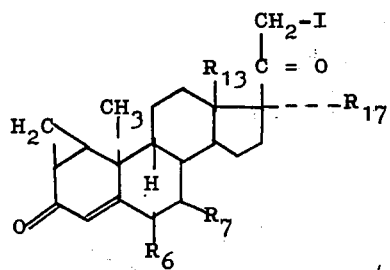

wherein R$_7$, R$_{13}$, R$_{17}$ have the aforesaid meanings and R$_6$ is a hydrogen atom, a fluorine atom or a methyl-group, with AgF in a solvent, which results in the corresponding 21-F-compound, i. treating a compound of the formula:

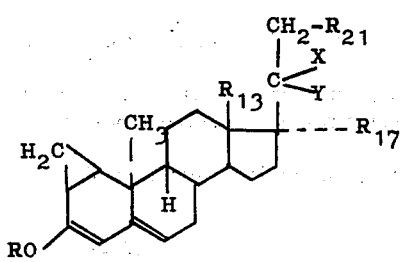

wherein
R$_{13}$, R$_{17}$, R$_{21}$, X and Y have the aforesaid meanings and
OR is an etherified or an esterified hydroxy-group, with a chlorating or fluorating agent, which results in a compound of the formula:

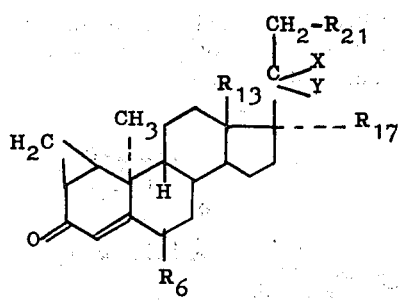

wherein
R$_{13}$, R$_{17}$, R$_{21}$, X and Y have the aforesaid meanings and
R$_6$ is a chlorine atom or a fluorine atom, j. subjecting a compound of the formula:

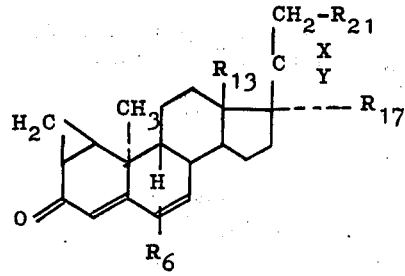

wherein R$_{13}$, R$_{17}$, R$_{21}$, X and Y have the aforesaid meanings, with the exception of the combination R$_{17}$ and/or R$_{21}$, being an esterified hydroxy-group and X and Y are in common a double-bonded oxygen atom and R$_6$ is a hydrogen atom, a chlorine atom or a fluorine atom, to a methylation reaction, which results in a compound of the formula:

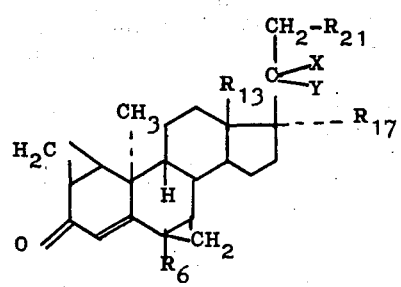

in which R$_6$, R$_{13}$, R$_{17}$, R$_{21}$, X and Y have the aforesaid meanings, k. treating a compound of the formula:

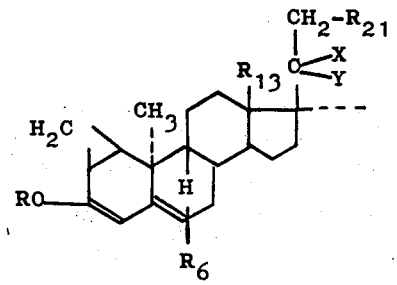

wherein
R$_6$, R$_{13}$, R$_{17}$, R$_{21}$, X and Y have the aforesaid meanings,
R$_6$ is a chlorine atom or a fluorine atom and
OR is an etherified group,
with a chlorating agent, if R$_6$ is a chlorine atom or with a perchlorylfluoride, if R$_6$ is a fluorine atom, which results in a compound of the formula:

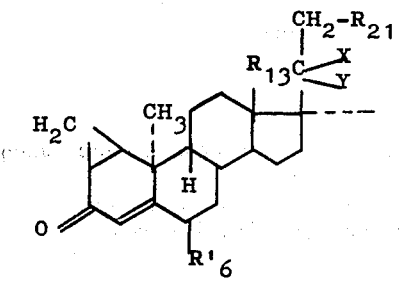

wherein
R$_{13}$, R$_{17}$, R$_{21}$, X and Y have the aforesaid meanings and
R'$_6$ is a 6,6-dichloro- or 6,6-difluoro-group,
l. treating a compound of the formula:

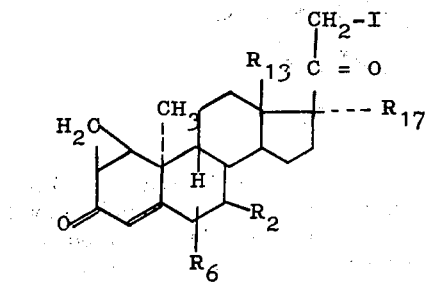

wherein R$_7$, R$_{13}$ and R$_{17}$ have the aforesaid meanings and R$_6$ is a hydrogen atom, a methyl-group or a fluorine atom, with triethylamine acetic acid and subsequently with an alkaline metal acetate, which results in the corresponding 21-acetate compound;

m. hydrolysing a compound of the formula:

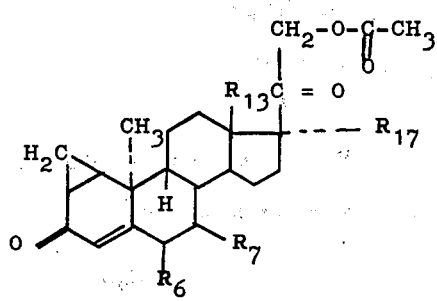

wherein R$_7$, R$_{13}$ and R$_{17}$ have the aforesaid meanings and R$_6$ is a hydrogen atom, a fluorine atom or a methyl-group, which results in the corresponding 21-OH-compound, n. catalytically hydrogenating a compound of the formula:

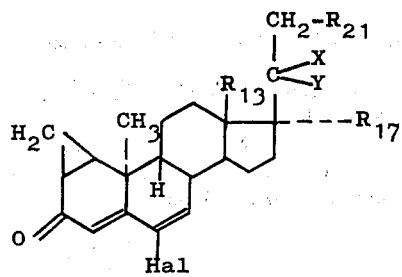

wherein
R$_{13}$, R$_{17}$, R$_{21}$, X and Y have the aforesaid meanings, and
Hal is a chlorine atom or a fluorine atom, which results in a compound of the formula:

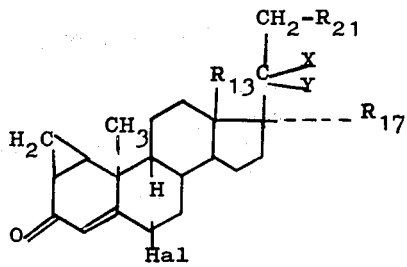

wherein R$_{13}$, R$_{17}$, R$_{21}$, X and Y and Hal have the aforesaid meanings, o. catalytically hydrogenating a compound of the formula:

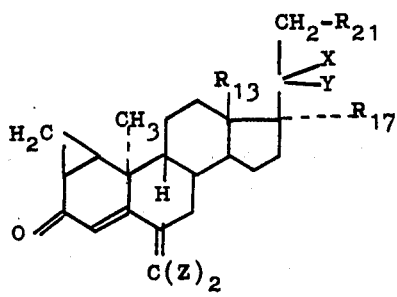

wherein
R$_{13}$, R$_{17}$, R$_{21}$, X and Y have the aforesaid meanings and
Z is a hydrogen atom, a chlorine atom or a bromine atom, which results in the corresponding 6-methyl compound, p. isomerising a compound of the formula:

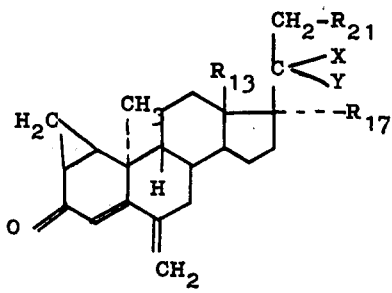

wherein R$_{13}$, R$_{17}$, R$_{21}$, X and Y have the aforesaid meanings, in the presence of a solvent, which results in a compound of the formula:

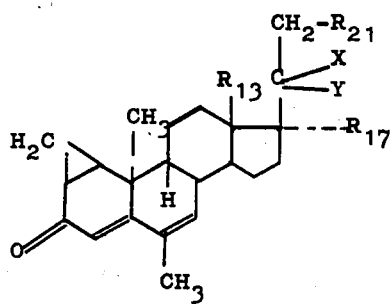

wherein $R_{13}$, $R_{17}$, $R_{21}$, X and Y have the aforesaid meanings, q. treating a compound of the formula:

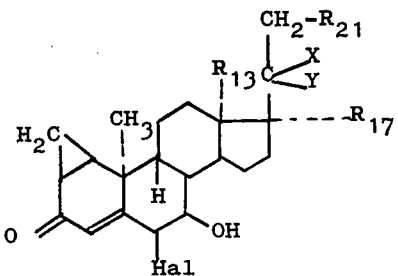

wherein $R_{13}$, $R_{17}$ have the aforesaid meanings,

X and Y in common represent a double-bonded oxygen atom, or X is a hydrogen atom and Y is an esterified hydroxy-group, $R_{21}$ is a hydrogen atom, a fluorine atom or an esterified hydroxy-group, and Hal is a fluorine atom or a chlorine atom, with a dehydrating agent, which results in a compound of the formula:

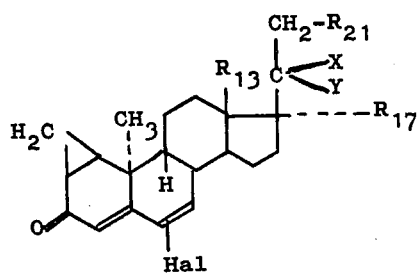

wherein $R_{13}$, $R_{17}$, $R_{21}$, Hal, X and Y have the aforesaid meanings.

The methods mentioned sub $a$ to $q$ are described in detail hereinafter. Where reference is made to literature, this means that the process concerned is analogous to the process described in the literature.

Ad a

Suitable acylating agents are carboxylic acids, carboxylic acid anhydrides or carboxylic acid chlorides in the presence of a catalyst such as p-toluene sulphonic acid, trifluoroacetic acid, anhydride or pyridine-HCl or in the presence of an acid binder such as an organic base, for example, collidine.

The acylating reaction is carried out in the presence of a solvent such as a hydrocarbon, for example, benzene or toluene.

The reaction temperature may vary between room temperature and the boiling point of the solvent used. If the starting material of method $a$ contains, apart from the 17-OH-group, one or more further OH-groups, they will also be esterified.

The alkylating reaction may be carried out by the following methods:

1. A reaction with an alkylhalide or aralkylhalide in the presence of $Ag_2O$.
2. A reaction of dihydropyrane or dihydrofurane in a weak acidic, weak alkaline or neutral medium.

The starting materials of method $a$ may be obtained by reacting a compound of the formula:

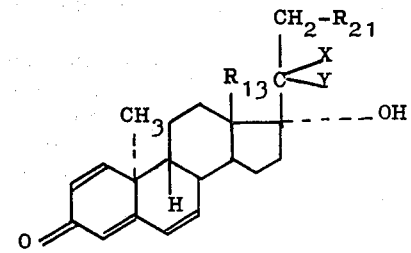

wherein $R_{13}$, $R_{21}$, X and Y have the aforesaid meanings, with the exception that the combination $R_{21}$ is an esterified hydroxy-group and X and Y are a double-bonded oxygen atom, with dimethylsulphoxonium-methylide and by subsequently introducing into the resultant 1,2-methylene compound the desired substituent such as, for example, a 6,7-$CH_2$-group, a 6-Cl-group, a 6-$CH_3$-group or a 6-Cl-6,7-$CH_2$-group.

The aforesaid introduction of a 1,2-methylene-group is performed more rapidly with higher yields, if the 17-OH-group contained in the starting material is protected during the reaction by dimethylsulphoxonium-methylide.

Protection of the 17-OH-group is performed by conversion into an ether-group, which can be readily removed by hydrolysis after the termination of the reaction. It has been found that a suitable 17-ether group is the 17-tetrahydropyranyloxy-group. This group is introduced by treating the 17-OH-starting material with dihydropyrane in a weak acid, alkaline or neutral medium. The reaction with dihydropyrane is performed particularly satisfactorily in the presence of p-tosyl-alcohol as a catalyst and also as a solvent. The 17-tetrahydropyranyloxy-group may be converted by hydrolysis into the 17-OH-group. For the production of the starting materials reference is made to the Examples.

Ad b

The same acylating agent as mentioned above sub Ad $a$ may be employed, if the starting material contains a plurality of hydroxy-groups, which will also be etherified.

Ad c

The esterification is carried out with the aid of a carboxylic acid chloride or anhydride in the presence of a base such as pyridine or collidine. Hydroxy-groups, if any, at the 3- or 21-positions will also be esterified.

Ad d

The esterification is carried out with a carboxylic acid chloride or anhydride in the presence of a base such as pyridine or collidine. The esterification takes place by the treatment with an alcohol in the presence of a catalytical quantity of acid such as HCl. The starting product of method $d$ is produced by reducing the corresponding compound containing a 3-keto oxygen atom. Reduction to the 3-OH-group may be performed by a treatment with $NaBH_4$ in methanol or tetrahydrofurane at low temperatures (0°C) or with $LiAlH(t.OBu)_3$.

Ad e

The introduction of a $\Delta^6$ double bond

A 6,7-double bond may be introduced by means of the following processes:

a. By direct 6-dehydrogenation of 3-keto-$\Delta^4$-9$\beta$, 10$\alpha$-steroids.
  1. with substituted benzoquinones such as chloranyl, (E. J. Agnello and G. D. Laubach: J. Am. Chem. Soc. 82 (1960, or 2,3-dichloro-5,6-dicyanobenzoquinone; (Bowers: J. Am. Chem. Soc. 81 5991 (1959) (H. J. Ringold and A. Turner: Chem. and Ind. 1962 211),
  2. with manganese dioxide (F. Sondheimer c.s. J. Am. Chem. Soc. 75 5932 (1953),
b. By reaction of $\Delta^{3,5}$-3-enolether-6-halosteroid with a halogen-substituted benzoquinone such as 2,3-dichloro-5,6-dicyanobenzoquinone,
c. Oxidation of 3-enolether-$\Delta^{3,5}$-6-halo steroids with tert. butylchromate or with manganese dioxide in acetic acid, which yields 3-keto-$\Delta^{4,6}$-halosteroids (K. Yasuda: Chem. Pharm. Bull. 1167 (1963 and H. Els c.s.: Helv. Chem. Acta 48 989 (1965).
d. By halogenation of a $\Delta^{3,5}$-3-enolether (or ester)-compound having a halogen atom or a methyl-group at the 6-position, followed by dehydrohalogenation, which results in a 3-keto-4,6-bisdehydro-6-halocompound.

The halogenation of a $\Delta^{3,5}$-3-enolether compound may be carried out with a halogen such as bromine or chlorine.
(L. H. Knox- J. Am. Chem. Soc. 82 1230(1960) or with N-haloimides such as bromosuccinicimide (the same literature). The halogenation of a $\Delta^{3,5}$-3-enolester compound may also taken place with the aid of a halogen (H. H. Inhofen C. P. 53 456 (1959) or with N-haloimides (C. Djerassi: J. Am. Chem. Soc. 77 3827 (1959).

The dehydrogenation is preferably carried out by a reaction with organic base such as pyridine or collidine.

ad *f*

Introduction of a 3-enolether (or 3-enolester) -$\Delta^{3,5}$-system
a. by enoletherification of a 3-keto-$\Delta^4$-steroid with an orthoformate ester in the presence of a catalyst, for example, ethylorthoformate and hydrochloride, (A. Serini c.s. Ber. 71 1766 (1938) or ethylorthoformate with p-toluene sulphonic acid. (R. Gardi c.s. J. Org. Chem. 27 668 (1962) and A. D. Cross c.s. Steroids 6 198 (1963).
b. Enolesterification may be performed by means of, for example, isopropenylacetate in the presence of an acid catalyst, such as p-toluene sulphonic acid or sulphuric acid or by means of an acid anhydride in the presence of, for example, p-toluene sulphonic acid.

If the starting compound contains one or more hydroxy-groups they will also be esterified.

Ad *g*

A 20-keto oxygen atom may be reduced, for example, by $LiAlH_4$ or an alkali-metal in the presence of an alcohol, such as absolute ethanol or propanol-2. Since a 3-keto oxygen atom is also reduced under these conditions, the reduction reaction has to be followed by selective oxidation, in which the 3-OH-group is oxidized to a 3-keto-oxygen atom. Suitable oxidation agents are substituted benzoquinones such as 2,3-dichloro-5,6-dicyanobenzoquinone.

Ad *h*

The reaction is carried out in an a-protic solvent such as acetone, acetonitrile. The reaction is preferably carried out in the presence of calciumfluoride, whilst for example the $CaF_2$ forms the carrier material on which the reagent AgS is suspended. The starting material of method *g* is produced by reacting a corresponding 21-$CH_3$ compound with $J_2/CaO$ in methanol at a temperature of about 30°C.

Ad *i*

Introduction of a 6-chloro- or 6-fluoro-atom
a. by chlorination of fluorination of a $\Delta^{3,5}$-3-enolether steroid with chlorine (L. H. Knox: J. Am. Chem. Soc. 82 1230 (1960), chlorosuccinic imide or perchlorylfluoride (S. Nakanischi: J. Am. Chem. Soc. 81 5259 (1959).
b. by chlorination or fluorination of $\Delta^{3,5}$-3-enolsteroid with chlorine (H. H. Imhofen C.A. 53 456 (1959) or chlorosuccinic imide (C. Djerassi H. Am. Chem. Soc. 77 3827 (1955) or with perchlorylfluoride. (B. M. Bloom: Chem. and Ind. 1959 1317).

Ad *j*

Introduction of a 6,7-methylene-group
The methylenation is carried out with dimethylsulphoxoniummethylide in the presence of an a-protic solvent.

Suitable solvents are, for example, ethers such as dioxane or tetrahydrofurane and dimethylsulphoxide.

The reaction temperature may vary between 0° and 80°C and it is preferably 15° to 30°C.

The reagent is produced by treating trimethylsulphoxoniumiodide with a base such as an alkali-hydride in the presence of a solvent such as dimethylsulphoxide.

Ad *k*

Suitable chlorinating agents are, for example, chlorine and chlorosuccinic acid imide or n-dichlorobenzenesulphonamide.

Ad *l*

The reactions are carried out in a solvent such as a ketone, for example, acetone. The reaction temperature is preferably equal to the boiling point of the solvent employed.

Ad *m*

The hydrolysis is carried out under mild conditions in order to avoid hydrolysis of the substituent $R_{17}$. A satisfactory hydrolysis can be carried out with an alkalimetal carbonate in the presence of methanol and water.

Ad *n*

The catalytic hydrogenation is preferably carried out with the catalyst palladium suspended, for example, on $CaCO_3$, $SrCO_3$, $BaSO_4$ or carbon. The reaction takes place in the presence of a solvent such as an aromatic hydrocarbon, for example, benzene or toluene.

Ad *o*

The catalytic hydrogenation may be carried out with the catalyst palladium suspended, for example on $CaCO_3$, $SrCO_3$, $BaSO_4$ or carbon.

The starting material for method *o* in which Z is a hydrogen atom is obtained by treating a corresponding steroid not containing a 6-substituent with pyrrolidine and by subsequently treating the resultant 3-enamine-3,5-bisdehydro-steroid with metaldehyde in ethanol-benzene and by finally dehydrating the resultant 3-keto-4-dehydro-6-hydroxymethyl compound.

The starting substances for method *o* in which Z is a chlorine or bromine atom are produced by reacting a 3-alkoxy-3,5-diene-9,$\beta$,10$\alpha$-steroid with tetrahalomethane for example, trichloromonobromomethane or with tetrabromomethane and by subsequently separating out hydrochloride or hydrobromide from the resultant 3-keto-4-dehydro-6-trichloro (or tribromo)-methyl-9$\beta$,10$\alpha$-steroid. The latter reaction is preferably carried out with an alkalialkoxide in an alcohol, for example, sodiummethoxide in boiling methanol or an alkaline anion exchanger of the Dowex I type.

Ad *p*

The isomerisation is carried out with palladium as a catalyst in a reaction medium containing inter alia cyclohexene, sodium-acetate and absolute ethanol (solvent), The reaction temperature corresponds to the boiling point of the solvent employed.

Ad *q*

The dehydration may be carried out, for example, with hydrochloride or hydrobromide in a solvent such as dioxane (K. Brückner. Chem. Ber. 94 1225 (1961). The starting compounds of method *q* may be obtained by the reaction of a 3-keto- $\Delta$ $^{4,6}$-steroid with chromylchloride or by reacting a 3-keto-$\Delta$ $^{4,6}$-steroid with an organic per-acid, for example, monoperphthalic acid, in accordance with a process described by Brückner: (Chem. Ber. 94 1225 (1961), where the corresponding 6,7-epoxide is formed, followed by a reaction with hydrochloride or hydrofluoride.

Apart from the above-mentioned progestational and antiovulatory activity the compounds according to the invention also exhibit high deciduom-building properties. The compounds are furthermore anti-estrogenic and moreover, capable of maintaining pregnancy and inducing ovulation.

On the basis of their endocrinological activity the substances according to the invention are suitable for the following uses:

As contraceptive for maintaining pregnancy, for combating habitual or iminent abortus, for combating sterility, acne, hirsutism, dysmenorrhea, menorrhagiene, oligoand polymenorrhea, primary and secondary amenorrhea, hyperand hypomenorrhea, for combating pre-menstrual tensions and for inducing ovulation.

A very important and interesting possibility of use of the preparations according to the invention is the aforesaid anti-fertile use. The method of treating in an anti-fertility system of the preparations according to the invention does, in principle, not deviate from the methods generally used in this field.

In accordance with the classical method preparations according to the invention, containing in addition an estrogenic compound, can be administered daily in the form of a tablet. In order to carry out a sequential method the combined preparation according to the invention may be administered for part of the menstrual cycle, for example, daily for five days and for a different part of the cycle an estrogenic substance. It is, however, advantageous to use the preparations according to the invention in the so-called "low-progestation treatment." In accordance with this method a progestational substance is administered periodically, for example, daily during the cycle. Since in this method, in which no estrogen is used, it is important to have a highly active progestative available, the highly active preparations according to the invention will offer direct advantageous.

Said quantity of active substance per dosage unit of the preparation according to the invention can be further defined as follows in dependence upon the anti-fertility method used:

A. Classical anti-fertility method:

Dosage rate: daily administration of one tablet for the duration of the cycle.

Tablet composition: 0.01 to 1 mg of 1,2-methylene-6-fluoro-17$\alpha$-hydroxy-9$\beta$,10$\alpha$-pregna-4,6-diene-3,20-dione 17-acetate. 0.01 to 1 mg of ethinylestradiol completed with carrier material and adjuvants to a tablet weight of 300 mgs.

b. Sequential method:

Dosage rate:
1. daily administration of one tablet for 5 days of the cycle.
2. daily administration of one tablet for 15 to 16 days of the cycle.

Composition of tablets: The tablet sub (1) has the same composition as indicated sub (a). The tablet sub (2) contains 0.05 to 0.1 mg of mestranol, completed with carrier material and adjuvants to a tablet weight of 30 to 300 mgs.

c. "Low-progestagen treatment":

Dosage rate: daily administration of one tablet for the duration of the cycle.

Tablet composition: 0.001 to 0.1 mg of 1,2-methylene6-fluoro-17$\alpha$-hydroxy-9$\beta$,10$\alpha$-pregna-4,6-diene-3,20-dione 17-acetate, completed with carrier material and adjuvants to a tablet weight of 30 to 300 mgs.

Instead of using the said oral preparations, injection preparations may also be employed.

An injection preparation according to the invention may be administered once in three months and it contains 0.1 to 1 mg of an active compound according to the invention.

The preparations according to the invention may be produced by mixing the active substance with solid carrier material or by dissolving or dispersing it in liquid carrier material, if desired, with the addition of adjuvants such as lubricants, binders, desintegration agents, surface-active substances and solvents.

The combination preparations according to the invention are obtained by adding also a known endocrinologically active substance such as an estrogenic substance to the constituents to be mixed, dissolved or dispersed.

Suitable solid carrier materials for oral preparations such as tablets and drageers are, for example: disaccharides and polysaccharides such as saccharose, lactose, glucose, dextrose, cellulose and cellulose derivatives such as carboxylmethyl cellulose, methylcellulose, ethyl cellulose, hydroxyethyl cellulose and hydroxypropyl cellulose, alginic acids, salts of alginic acids and hemi-celluloses such as gelactomannan.

Suitable liquid carrier materials for injection preparations are, for example, arachis oil, cesam oil, soya oil, olive oil and mixtures of these and similar vegetable oils, furthermore isopropylmeristate and ethyloleate.

Suitable binders are, for example, gelatine, pectine, amylose, agar-agar, tragacanth, polyethylene glycols, arabic gum and polyvinylpyrolidone. Suitable desintegration agents are, for example, aminopectines, starches such as corn starch, potato starch and rice starch, formaline, caseine, bentonite, silicon dioxide and ion exchangers. Lubricants suitable for this purpose may be: polyethylene glycols, stearic acid, salts of stearic acid such as magnesium stearate and aluminum stearate.

Surface-active substances suitable for this purpose are, for example; wetting agents such as sodium dioctylsylphosuccinate, sodium laurylsulphate, polyoxyethylene sorbitan monolaureate, polyoxyethylene alkylethers and sulfated cetyloleylalcohol.

Suitable solvents for the production of injection preparations are methylene chloride and benzylalcohol. Tablets and dragees according to the invention may be obtained by mixing the active substance in the desired quantity with solid carrier material such as a carrier of the kind mentioned above, together with adjuvants such as a starch, magnesium stearate and talcum. The mixture thus obtained is homogenized and worked up to tablets or dragees.

The tablets or dragees may, if desired, be provided with a sugar layer consisting, for example, of the following ingredients: talcum, gelatine, arabic gum, potato starch, saccharose and a colorant. Instead of a sugar coating a different film-former may be used, such as for example, ethylcellulose and polyacrylate. Injection liquids may be obtained by dissolving the active substance in methylene chloride, by absorbing the solution in arachis oil and by subsequently evaporating the solvent. Ampullae and flasks are filled with the resultant solution, dealed and finally sterilized by heating at 120°C for some time.

Further particulars of the composition of the preparations according to the invention will be found in the Examples.

EXAMPLES

1. Production of 1,2-methylene-6-chloro-17α-hydroxy-9β,10α-pregna-4,6-diene-3,20-dione 17-acetate.

In a nitrogen atmosphere, at a temperature of −20°C, a solution of 10.1 ml of chromylchloride in 67 ml of methylene chloride is added to a thoroughly stirred solution of 6 g of 1,2-methylene-17α-hydroxy-9β,10α-pregna-4,6-diene-3,20-dione 17-acetate in 280 ml of methylene chloride, cooled at −20° C. After a reaction time of 2.5 hours the reaction mixture is poured out in a solution of 43 g of sodium acetate and 75 g of sodium bisulphite in 1 liter of water and subsequently it is extracted from methylene chloride and ethylacetate. The organic extract is washed with water and subsequently dried on sodium sulphate, the solvents being then evaporated and the residue being chromatographed on silicagel. The resultent 6-chloro-7-hydroxy compound is dissolved in 23 ml of dry dioxane and treated with 19 ml of dioxane for 3 hours, containing 23 mg of HCl per ml. The reaction mixture is diluted with glacial water, extracted from methylene chloride, then neutralized and dried, after which the solvent is evaporated and the residue is chromatographed. Recrystallisation yields pure 1,2-methylene-6-chloro-17α-hydroxy-9β,10α-pregna-4,6-diene-3,20-dione 17-acetate. Melting point 243° to 244°C.

2. Production of 1,2;6,7-bismethylene-6-chloro-17α-hydroxy-9β,10α-pregna-4-ene-3,20-dione 17-acetate.

a. 1,2-methylene-6-chloro-17α-hydroxy-9β,10α-pregna-4,6-diene-3,20-dione. 11.5 g of 1,2-methylene6-chloro-17α-hydroxy-9β,10α-pregna-4,6 diene-3,20-dione 17-acetate is added to a solution of 11 g of sodium perchlorate in 1100 ml of 0.5N methanol sodium hydroxide solution. The mixture is stirred in a nitrogen atmosphere at room temperature for 3 hours, then poured out in water and then extracted from methylene chloride. The extract is washed with water and dried on sodium sulphate, after which the solvent is evaporated and the residue is purified chromatographically. Yield 6 g of pure 1,2-methylene-6-chloro-17α-hydroxy-9α,10α-pregna-4,6-diene-3,20-dione, melting point of 219° to 219.5°C.

b. A solution of dimethylsulphoxonium methylide obtained by reacting 5 g of trimethylsulphoxonium iodide with 1.35 g of sodium hydride in 100 ml of dimethylsulphoxide is added to a solution of 5 g of the compound mentioned sub (a) in 100 ml of dimethylsulphoxide. The mixture is stirred in a nitrogen atmosphere for one hour at room temperature and then poured out in glacial water. Then the mixture is extracted from methylene chloride and the extract is subsequently washed with 0.1N-NaOH solution and water. The extract is then dried and the solvent is evaporated. The resultant crude 1,2;6,7-bismethylene-6chloro-17α-hydroxy-9β,10α-pregna-4-ene-3,20-dione can be used for the next reaction step without purification. Melting point of the pure substances is 230° to 231.5°C.

c. 5.2 G of the aforesaid reaction product is dissolved in 50 ml of acetic acid and 8 ml of acetic acid anhydride. After the addition of 2.5 g of p-toluene sulphonic acid the reaction mixture is stirred at room temperature for 1 hour, then pured out in glacial water and then extracted from methylene chloride. The extract is subsequently washed with water, water with a slight supply of pyridine, 2N sulphuric acid, water, sodium bicarbonate solution and water. After drying of the extract on sodium sulphate, the solvent is evaporated and the residue is chromatographed on silicagel. By crystallisation pure 1,2;6,7-bismethylene-6-chloro-17α-hydroxy-9β,10α-pregn-4-ene-3,20-dione 17-acetate is obtained, having a melting point of 203° to 205°C.

3. Production of 1,2;6,7-bismethylene-17α-hydroxy-9β,10α-pregn-4-ene-3,20-dione 17-acetate.

a. 1,2-methylene-17α-hydroxy-9β,10α-pregn-4,6-diene-3,20-dione.

A reaction mixture containing 17.3 g of dimethylsulphoxonium iodide and 3.18 g of sodium hydride (50% of oil suspension) in 130 ml of dimethylsulphoxide is filtered and then added to a solution of 13.3 g of 17α-hydroxy-9β,10α-pregna-1,4,6-triene-3,20-dione in 300 ml dimethylsulphoxide. The mixture is stirred at room temperature in a nitrogen atmosphere for 5.5 hours, then decanted in glacial water and subsequently extracted from benzene-ether. After further processing recrystallisation provides the pure substance mentioned above. Melting point 231°C.

b. A solution of 4 g of the compound mentioned above sub a) in 50 ml of dimethylsulphoxide is added to a solution of dimethylsulphoxoniummmethylide, the latter being obtained by reacting 6.2 g of trimethylsulphoxonium iodide with 0.95 g of sodium hydride (50% oil suspension) in 28 ml of dimethylsulphoxide. The reaction mixture is kept at room temperature for 70 hours and then worked up by conventional methods.

After chromatographing on silicagel pure 1,2;6,7-bis-methylene-17α-hydroxy-9β,10α-pregn-4-ene-3,20-dione is obtained, which is then converted in the manner described under Example 2c into 1,2;6,7-bismethylene-17α-hydroxy-9β,10α-pregn-4-ene-3,20-dione 17-acetate. Melting point 274° to 276°C.

4. Production of 1,2-methylene-6-fluoro-17-hydroxy-9β,10α-pregn-4-ene-3,20-dione 17-acetate.

a. 1,2-methylene-17α-hydroxy-9β,10α-pregn-4-ene-3,20-dione 17 acetate 3.7 G of 1,2-methylene-17α-hydroxy-9β,10α-pregna-4,6-diene-3,20-dione is added to a hydrogenation mixture of 370 mg of palladium on CaCO₃ in 37 ml of toluene. After the absorption of the theoretical quantity of hydrogen the reaction mixture is filtered and the solvent is subsequently evaporated. The residue is recrystallized: yield 95% of pure 1,2-methylene-17α-hydroxy-9β,10α-pregn-4-ene-3,20-dione 17-acetate. Melting point 205° to 205.5°C.

b. A solution of 5 g of the substance mentioned sub (a) in 120 ml of acetic acid anhydride is kept, after the addition of 5 g of p-toluene sulphonic acid, at room temperature for 24 hours. The reaction mixture is then poured in water and the precipitate is filtered off. After recrystallisation of the crude product pure 1,2-methylene-3,17α-dihydroxy-9β,10α-pregna-3,5-diene-20-one 3,17-diacetate is obtained. Melting point 118° to 119°C.

c. Perchlorylfluoride is passed through a solution of 4.9 g of the substance mentioned above sub (b) in 250 ml of dioxane and 50 ml of water. After a reaction period of two hours no starting material is any longer found to be present. The reaction mixture is then stirred for 1 hour whilst nitrogen is led through. After the addition of water the reaction mixture is extracted from methylene chloride and the extracts are washed in order of succession with sodium bicarbonate solution and water. The extract is then dried on sodium sulphate, the solvent is evaporated and the residue is chromatographed. Crystallisation yields pure 1,2-methylene-6α-fluoro-17α-hydroxy-9β,10α-pregn-4-ene-3,20-dione 17-acetate having a melting point of 178° to 179°C and pure 1,2-methylene-6β-fluoro-17α-hydroxy-9β,10α-pregn-4-ene-3,20-dione 17-acetate having a melting point of 239° to 240°C.

5. Production of 1,2-methylene-6-fluoro-17α-hydroxy-9β,10α-pregna-4,6-diene-3,20-dione 17-acetate 4.2 Ml of ethylorthoformate in 160 mg of p-toluene sulphonic acid is added to a solution of 4.8 g of 1,2-methylene-6-fluoro-17α-hydroxy-9β,10α-pregn-4-ene-3,20-dione 17-acetate in 90 ml of dry dioxane.

The mixture is kept in darkness at room temperature for 20 hours. After cooling of the mixture to 0°C, 150 ml of glacial acetone solution of 1.7 g of sodium acetate in 17 ml of water, 4,1 g of m-bromosuccinic imide and 1.5 ml of acetic acid are added. The resultant mixture is stirred at 0°C for 30 minutes and poured out in water and subsequently extracted from methylene chloride. The extract is subsequently washed with water, a solution of NaOH in water and water, after which the extract is dried and the solvent is evaporated. The residue is absorbed in 20 ml of pyridine and heated at 90°C for 45 minutes. After processing and chromatographic purification substantially pure 1,2-methylene-6-fluoro-17α-hydroxy-9β,10α-pregna-4,6-diene-3,20-dione 17acetate is obtained. Melting point 249° to 251°C.

The last-mentioned product is also made by absorbing 1,2-methylene-6α-fluoro-17α-hydroxy-9β,10α-pregn-4-ene-3,20-dione 17-acetate is dioxane-HCl, after which it is reacted for 16 minutes with 2,3-dichloro-5,6-dicyanobenzoquinone in dioxan-HCl. (130 mg HCl/ml dioxane).

The product is also obtained by treating a solution of 1,2-methylene-6-fluoro-17α-hydroxy-9β, 10α-pregn-4-ene-3,20-dione 17-acetate in dry dioxane with ethylorthoformate and p-toluene sulphonic acid after which the resultant 3-ethoxy-3,5-bisdehydro-bound is reacted for three hours with McO₂ in acetic acid.

6. Production of 1,2-methylene-6-methyl-17α-hydroxy-9β,10α-pregna-4,6-diene-3,20-dione 17-acetate a. 1,2-methylene-17α-hydroxy-9β,10α-pregna-4-ene-3,20-dione 3.7 G of 1,2-methylene-17α-hydroxy-9β,10α-pregna-4,6-diene-3,20-dione is added to a hydrogenation mixture of 370 mg of palladium on CaCO₃ in 37 ml of toluene. After the absorption of the theoretical quantity of hydrogen the reaction mixture is filtered and the solvent is subsequently evaporated. The residue is recrystallized, yield 95% of pure 1,2-methylene-17α-hydroxy-9β,10α-pregn-4-ene-3,20-dione.

b. 1,2-methylene-6,6-dichloro-methylene-17α-hydroxy-9β,10α-pregn-4-ene-3,20-dione.

To a solution of 3.7 g of the compound mentioned above sub (a) in 52 ml of dry dioxane are added 2.3 ml of ethylorthoformate and 52 mg of p-toluene-sulphonic acid, after which the mixture is kept in darkness for 27 hours. Then 1.5 ml of pyridine and 5.5 ml of trichlorobromomethane are added and the mixture is exposed to day light for 7 days. The reaction mixture is filtered, the filtrate is diluted with 500 ml of 2N-HCl solution, extracted and the extract is washed in order of succession with water, sodium bicarbonate solution with water. After drying on silicagel the solvent is evaporated. The residue formed by 1,2-methylene-6-trichloromethyl-17α-hydroxy-9β,10α-pregn-4-ene-3,20-dione.

c. 3 G of 1,2-methylene-6-trichloromethyl-17α-hydroxy-9β,10α-pregn-4-ene-3,20-dione is added to a chronium(II) chloride solution obtained by reacting 15 g of chromium (III)-chloride and 12 g of zinc in 105 ml of ethanol and 22.5 ml of hydrochloric acid. The mixture is stirred at room temperature is a nitrogen atmosphere for 45 minutes, then poured out in water and subsequently extracted from methylene chloride. The extract is washed in order of succession with water, 5% sodium bicarbonate solution and water and subsequently dried. After the evaporation of the solvent the residue is chromatographed and subsequently crystallized, the yield being pure 1,2;6-bismethylene-17β-hydroxy-9β,10α-pregn-4-ene-3,20-dione.

d. 1,2-methylene-6-methyl-17α-hydroxy-9β,10α-pregna-4,6-diene-3,20-dione 0.5 G of palladium on carbon is added in a nitrogen atmosphere to a boiling, thoroughly stirred solution of 2.5 g of the above-mentioned compound and 2.5 g of sodium acetate in absolute ethanol. To the mixture is added a 1% solution of cyclohexene in ethanol at a rate of 6 ml an hour. After a reaction time of about 3.75 hours the starting material is found to be converted into the 6-methyl-compound (U.V. measurements). The reaction mixture is then filtered and diluted with water, after which the precipitate is filtered off and dried. By chromatographic purification and subsequent crystallisation pure 1,2-methylene-6-methyl-17α-hydroxy-9β,10α-pregna-4,6-diene-3,20-dione is obtained.

e. The product mentioned sub (d) is esterified in the same manner as described in Example 2c into 1,2-methylene-6-methyl-17α.hydroxy-9β,10α-pregna-4,6-diene-3,20-dione 17-acetate.

7. Production of 1,2-methylene-6-methyl-17α-hydroxy-9β,10αpregna-4,6-diene-3,20-dione 17-caproate The product mentioned in Example 6d is dissolved in a mixture of capronic acid and trifluoro-acetic acid anhydride, after which the mixture is heated in a nitrogen atmosphere at 60°C for 45 minutes. After dilution with water, the mixture is extracted from methylene chloride and the extract is washed in order of succession with water, 5% sodium bicarbonate solution and water. The solvent is subsequently evaporated and the residue is chromatographed. Crystallisation yields pure 1,2-methylene-6-methyl-17α-hydroxy-9β,10α-pregna-4,6-diene-3,20-dione 17-caproate.

8. Production of 1,2-methylene-6-fluoro-17α-hydroxy-9β,10α-pregna-4,6-diene-3,20-dione 17-caproate 1,2-Methylene-6-fluor-17α-hydroxy-9β,10α-pregna-4,6-diene-3,20-dione 17-acetate (see Example 5) is hydrolysed in the same manner as described in Example 2a into 1,2-methylene-6-fluoro-17α-hydroxy-9β,10α-pregna-4,6-diene-3,20-dione. The latter compound is then esterified with capronic acid in the manner described above in Example 7, the result being 1,2-methylene-6-fluoro-17α-hydroxy-9β,10α-pregna-4,6-diene-3,20-dione 17-caproate. In a similar manner is also produced 1,2-methylene-6-fluoro-17α-hydroxy-9β,10α-pregna-4,6-diene-3,20-dione 17-propionate having a melting point of 179° to 180°C.

9. Production of 6-chloro-17α-hydroxy-9β,10α-pregna-4,6-diene-3,20-dione 17acetate a. To a stirred solution of 4 g of 3,17α-dihydroxy-1,2-methylene-9β,10α-pregna-3,5-diene-20-one 3,17-diacetate (see Example 4) in 75 ml of ether is added at 0°C a solution of 7.5 g of potassium acetate in 175 ml of acetic acid and 30 ml of water and a solution of 1.1 eq. of chlorine in 14 ml of acetic acid. After agitation at 0°C for 30 minutes the mixture is processed by pouring it out in water and extracting it from ether. The ether extract is washed in order of succession with water, 5% sodium bicarbonate solution and water. The product obtained subsequent to drying and evaporation to dryness is chromatographed on silicagel and then crystallized. The yield is pure 6β-chloro-17α-hydroxy-1,2-methylene-9β,10α-pregn-4-ene-3,20-dione 17-acetate, having a melting point of 222.5° to 223°C.

b. To a solution of 2 g of 6β-chloro-17α-hydroxy-1,2-methylene-9β,10α-pregn-4-ene-3,20-dione 17-acetate in 35 ml of dry dioxane are added 1.9 ml of ethylorthoformate and 0.075 g of p-toluene sulphonic acid. The solution is kept in darkness for 20 hours. The resultant 6-chloro-3-ethoxy-17α-hydroxy-1,2-methylene-9β,10α-pregna-3,5-diene-20-one 17-acetate is suitable for the next step without the need for further purification.

c. The solution of the 6-chloro-3-ethoxy-17α-hydroxy-1,2-methylene-9β,10α-pregna-3,5-diene-20-one 17-acetate obtained as described sub (b) is added to a stirred suspension of 12 g manganese dioxide in 100 ml of acetic acid and 12 ml of water. After one hour the mixture is filtered and the filtrate is concentrated in vacuo. The residue is dissolved in methylene chloride and the solution is washed in order of succession with water, 5% sodium bicarbonate solution and water. After drying and evaporation to dryness the resultant residue is chromatographed, the yield being pure 6-chloro-17α-hydroxy-1,2-methylene-9β,10α-pregna-4,6-diene-3,20-dione 17-acetate; melting point 244° to 245°C.

10. Production of 6-chloro-3,17α-dihydroxy-1,2-methylene-9β,10α-pregna-4,6-diene-20-one 3,17-diacetate a. To a stirred solution of 1 g of 6-chloro-17α-hydroxy-1,2-methylene-9β,10α-pregna-4,6-diene-3,20-dione 17-acetate in a mixture of 20 ml of absolute dioxane and 57 ml of absolute methanol is added slowly in drops at 0°C a solution of 675 mg of sodium borohydride in 10 ml of water. After half an hour the excess quantity of sodium borohydride is decomposed by acetic acid and the reaction mixture is decanted into water. The water layer is extracted with three times 100 ml of methylene chloride and the organic layer is washed with water to neutral. After drying and filtering the solvent is distilled off at a reduced pressure and the residue is chromatographed on silicagel. The final yield is 6-chloro-3,17α-dihydroxy-1,2-methylene-9β,10α-pregna-4,6-diene-20-one 17-acetate.

b. 710 Mg of the resultant compound is dissolved in a mixture of 5 ml of absolute pyridine and 2 ml of acetic acid anhydride. After 24 hours at room temperature the reaction mixture is processed by the addition of ice and pouring out in water and shaking with methylene chloride. The organic layer is washed to neutral with 5% sodium bicarbonate solution and water. After drying and evaporation to dryness the residue is chromatographed on silicegel. Yield: 6-chloro-3,17α-dihydroxy-1,2-methylene-9β,10α-pregna-4,6-diene-20-one 3,17-diacetate.

11. Production of 3-ethoxy-6-fluoro-17α-hydroxy-1,2-methylene-9β,10α-pregna-3,5-diene-20-one 17-acetate A solution of 8.8 g of 6α(and 6β)-fluoro-17α-hydroxy-1,2-methylene-9β,10α-pregna-4-ene-3,20-dione 17-acetate and 2.5 g of p-toluene sulphonic acid in 165 ml of dry dioxane and 95 ml of ethylorthoformate is stirred in a nitrogen atmosphere at 20°C in darkness for 24 hours. The reaction mixture is then poured out in 2 liters of petroleum-ether (40° to 65°C) and 5 ml of pyridine and the solution is filtered through silicagel. Yield: 3-ethoxy-6-fluoro-17α-hydroxy-1,2-methylene-9β,10α-pregna-3,5-diene-20-one 17-acetate.

12. Production of 6,6-difluoro-17α-hydroxy-1,2-methylene-9β,10α-pregn-4-ene-3,20-dione 17-acetate A solution of 8.2 g of 3-ethoxy-6-fluoro-17α-hydroxy-1,2-methylene-9β,10α-pregna-3,5-diene-20-one 17-acetate in 160 ml of dry acetone is added to a solution of 4 g of dry potassium acetate in 110 ml of absolute ethanol. At 0°C this mixture has passed through it perchloryfluoride for 3 hours, whilst stirring. Subsequently nitrogen is led through for one hour, the solid substance being then filtered off and the filtrate being poured out in 1500 ml of glacial water. The mixture is extracted from methylene chloride and the extract is washed in order of succession with water, 5% sodium bicarbonate solution and water. After drying on sodium sulphate the solvent is evaporated and the residue is chromatographed on silicagel. Yield: pure 6,6-difluor-17α-hydroxy-1,2-methylene-9β,10α-pregn-4-ene-3,20-dione 17-acetate: melting point 196° to 198°C.

13. Production of 6-chloro-17α-hydroxy-1,2-methylene-9β,10α-pregna-4,6-diene-3,20-dione 17-propionate 0.35 G of 6-chloro-17α-hydroxy-1,2-methylene-9β,10α-pregna-4,6-diene-3,20-dione (see Example 2a) is esterified in a mixture of 14 ml of propionic acid and 3.5 ml of trifluoroacetic acid anhydride at 60°C within 1 hour. The reaction mixture is processed by pouring it out in water and extraction from methylene chloride. After washing to neutral, drying and evaporation in dryness the extract porvides a residue which yields, subsequent to chromatography on silicagel and crystallisation from methylene chloride-acetone pure 6-chloro-17α-hydroxy-1,2-methylene-9β,10α-pregna-4,6-diene-3,20-dione 17-propionate. Melting point 179° to 180°C.

14. Production of 6-fluoro-17α-methoxy-1,2-methylene-9β,10α-pregna-4,6-diene-3,20-dione A solution of 0.35 g of 6-fluoro-17α-hydroxy-1,2-methylene-9β,10α-pregna-4,6-diene-3,20-dione in 35 ml of dimethylformamide and 17.5 ml of methyliodide is stirred at 20°C for 70 hours in the presence of 3.5 g of silver oxide. Then the solid substance is filtered off and the filtrate is extracted subsequent to decanting in water, from methylene chloride and the resultant extract is evaporated to dryness after having been washed to neutral and subsequent to drying. The residue yields, subsequent to chromatography on silicagel, 6-fluoro-17α-methoxy-1,2-methylene-9β,10α-pregna-4,6-diene-3,20-dione.

By mixing the active substance(s) in a finely divided state with solid carrier material and adjuvants tablets and draggees of the following composition are made:

a. Tablet:

| | | |
|---|---|---|
| Active substance according to the invention for example, 1,2-methyl-6-fluoro-(or 6-chloro)-17α-hydroxy-9β,10α-pregna-4,6-diene-3,20-dione 17-acetate | 0.02 | mg |
| ethinylestradiol | 0.05 | mg |
| lactose | 56.2 | mg |
| powder sugar | 30.0 | mg |
| potato starch | 6.0 | mg |
| talcum | 6.7 | mg |
| magnesium stearate | 1.0 | mg |
| Total weight | 100.0 | mg |
| Tablet diameter: 6.3 mms. | | | b. Tablet:

| | | |
|---|---|---|
| Active substance according to the invention, e.g. 1,2-methylene-6-fluoro-(or 6-chloro)-17α-hydroxy-9β, 10α-pregna-4,6-diene-3,20-dione 17-acetate | 0.002 | mg |
| lactose | 25.0 | mg |
| corn starch | 6.0 | mg |
| microcrystalline cellulose | 6.0 | mg |
| talcum | 2.5 | mg |
| magnesium stearate | 0.5 | mg |
| Total weight | 40 | mg |
| Tablet diameter: 4 mms. | | | c. Dragee:

| | | |
|---|---|---|
| Core:substance according to the invention e.g. 1,2-methylene-6-fluoro-(or 6-chloro)-17α-hydroxy-9β,10α-pregna-4,6-diene-3,20.dione 17-acetate | 0.01 | mg |
| mestranol | 0.08 | mg |
| lactose | 35.0 | mg |
| saccharose | 15.0 | mg |
| corn starch | 5.0 | mg |
| talcum | 3.9 | mg |
| magnesium stearate | 1.0 | mg |
| Total core weight | 60.0 | mg |
| Coating: | | |
| talcum | 18.0 | mg |
| saccharose | 71.2 | mg |
| potato starch | 0.1 | mg |
| gelatine | 0.3 | mg |
| arabic gum | 0.3 | mg |
| carnaubawax | 0.02 | mg |
| shellack wax | 0.02 | mg |
| dammar resin | 0.03 | mg |
| | 90.0 | mg |
| Dragee weight | 150.0 | mg |

What is claimed is:

1. A compound of the formula

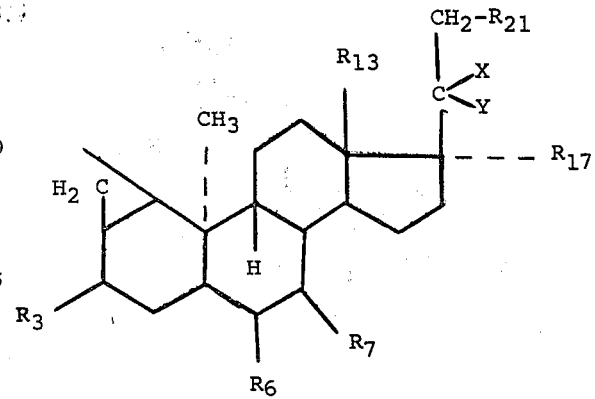

wherein X is hydrogen and Y is a member selected from the group consisting of hydroxy and esterified hydroxy of 1–20 carbon atoms derived from an acid containing only carbon, hydrogen and carboxylic moieties or X and Y together form a double bonded oxygen atom, $R_3$ is a member selected from the group consisting of 3-keto-4-dehydro, 3-keto-4,6-bisdehydro-, 3-OR'-3,5-bisdehydro and 3-OR'-4,6-bisdehydro wherein OR' is a member selected from the group consisting of esterified hydroxy of 1–20 carbon atoms derived from an acid containing only carbon, hydrogen and carboxylic moieties, methoxy, ethoxy, butoxy, cyclohexyloxy, benzyloxy, tetrahydrofuranyloxy and tetrahydropyranyloxy, $R_6$ is a member selected from the group consisting of hydrogen, chlorine, fluorine, 6,6-difluoro, 6,6-dichloro and methyl, $R_7$ is a member selected from the group consisting of hydrogen and 6,7-methylene with the proviso that $R_7$ is 6,7 methylene when $R_6$ is hydrogen and $R_6$ is a member of the group consisting of hydrogen, chlorine and fluorine and $R_3$ is 3-keto-4-dehydro when $R_7$ is 6,7-methylene, $R_{17}$ is a member of the group consisting of esterified hydroxy of 1 to 5 carbon atoms and esterified hydroxy of 1 to 8 carbon atoms derived from an acid containing only carbon, hydrogen and carboxylic moieties, $R_{21}$ is a member of the group consisting of hydrogen, fluorine, hydroxy and esterified hydroxy of 1 to 20 carbon atoms derived from an acid containing only carbon, hydrogen and carboxylic moieties, and $R_{13}$ is a member of the group consisting of methyl and ethyl.

2. A compound of the formula:

wherein Hal is chlorine or fluorine and $R_{17}$ is etherified hydroxy of 1–5 carbon atoms.

3. Compounds of the general formula:

in which $R_3$, $R_6$, $R_7$, $R_{17}$, $R_{21}$, X and Y have the meanings indicated in claim 1.

4. Compounds of the formula:

in which Hal is a chlorine atom or a fluorine atom and $R_{17}$ has the meaning given in claim 1.

5. 1,2-methylene-6-chloro-17α-hydroxy-9β,10α-pregna-4,6-diene-3,20-dione 17-acetate.

6. 1,2-methylene-6-fluoro-17α-hydroxy-9β,10α-pregna-4,6-diene-3,20-dione 17-acetate.

7. 1,2-methylene-6-fluoro-17α-hydroxy-9β,10α-pregna-4,6-diene-3,20-dione 17-propionate.

8. As a compound of claim 4, 1,2-methylene-6-chloro-17α-hydroxy-9β,10α-pregna-4,6-diene-3,20-dione 17-propionate.

9. 1,2-methylene-6-chloro-17α-tetrahydropyranyloxy-9β,10α-pregna-4,6-diene-3,20-dione.

10. 1,2-methylene-6-fluoro-17α-tetrahydropyranyloxy-9β,10α-pregna-4,6-diene-3,20-dione.

11. As a compound of claim 4, 1,2-methylene-6-fluoro-17α-methoxy-9β,10α-pregna-4,6-diene-3,20-dione.

12. As a compound of claim 4, 1,2-methylene-6-chloro-17α-methoxy-9β10α-pregna-4,6-diene-3,20-dione.

13. As a compound of claim 4, 1,2-methylene-6-chloro-17α-hydroxy-9β,10α-pregna-4,6-diene-3,20-dione 17-caproate.

14. As a compound of claim 4, 1, 2-methylene-6-fluoro-17α-hydroxy-9β,10α-pregna-4,6-diene-3,20-dione 17-caproate.

* * * * *